United States Patent
Goldman et al.

(10) Patent No.: US 9,042,966 B2
(45) Date of Patent: *May 26, 2015

(54) THREE DIMENSIONAL IMAGING OF VEINS

(71) Applicants: Ron Goldman, Cold Spring Harbor, NY (US); Fred Wood, Medford, NY (US); Stephen P. Conlon, Cold Spring Harbor, NY (US); Vincent Luciano, Shoreham, NY (US)

(72) Inventors: Ron Goldman, Cold Spring Harbor, NY (US); Fred Wood, Medford, NY (US); Stephen P. Conlon, Cold Spring Harbor, NY (US); Vincent Luciano, Shoreham, NY (US)

(73) Assignee: AccuVein, Inc., Cold Spring Harbor, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/276,139

(22) Filed: May 13, 2014

(65) Prior Publication Data

US 2014/0303506 A1    Oct. 9, 2014

Related U.S. Application Data

(63) Continuation of application No. 13/135,591, filed on Jul. 8, 2011, now Pat. No. 8,818,493, which is a continuation of application No. 11/823,862, filed on Jun. 28, 2007, now Pat. No. 7,983,738.

(51) Int. Cl.
*A61B 6/00* (2006.01)
*A61B 5/00* (2006.01)
(Continued)

(52) U.S. Cl.
CPC .............. *A61B 5/743* (2013.01); *A61B 5/0059* (2013.01); *A61B 5/489* (2013.01);
(Continued)

(58) Field of Classification Search
None
See application file for complete search history.

(56) References Cited

U.S. PATENT DOCUMENTS

| 3,527,932 A | 9/1970 | Thomas |
| 3,818,129 A | 6/1974 | Yamamoto |

(Continued)

FOREIGN PATENT DOCUMENTS

| FR | 2289149 | 5/1976 |
| GB | 1298707 | 12/1972 |

(Continued)

OTHER PUBLICATIONS

Wiklof, Chris, "Display Technology Spawns Laser Camera," LaserFocusWorld, Dec. 1, 2004, vol. 40, Issue 12, PennWell Corp., USA.

(Continued)

*Primary Examiner* — James Kish
(74) *Attorney, Agent, or Firm* — Thomas A. O'Rourke; Bodner & O'Rourke, LLP

(57) ABSTRACT

A three dimensional imaging system includes a first laser emitting light at a first wavelength, and a scanner for scanning the laser light in a pattern on the target area. A photo detector receives light reflected from the target area as a contrasted vein image, resulting from differential absorption and reflection therein of the first wavelength of light. The intensity of the first laser is incrementally increased, and the photo detector thereby receives a plurality of contrasted vein images, each being at incrementally distinct depths beneath the target skin surface. Image processing is performed on the plurality of vein images to successively layer the veins in the images according to their depth, to create a single processed vein image. A second laser emitting a second wavelength of light is used in combination with the scanner to project the processed vein image onto the target area to overlay the veins therein.

21 Claims, 11 Drawing Sheets

(51) Int. Cl.
  *A61M 5/42* (2006.01)
  *A61M 5/46* (2006.01)
  *A61B 19/00* (2006.01)

(52) U.S. Cl.
  CPC ........ *A61B 2019/5293* (2013.01); *A61M 5/427* (2013.01); *A61B 5/0037* (2013.01); *A61B 5/0075* (2013.01); *A61B 5/0082* (2013.01); *A61B 5/7475* (2013.01); *A61M 5/46* (2013.01); *A61B 5/0068* (2013.01); *A61B 5/0079* (2013.01)

(56) References Cited

U.S. PATENT DOCUMENTS

| | | | |
|---|---|---|---|
| 4,182,322 A | 1/1980 | Miller | |
| 4,185,808 A | 1/1980 | Donohoe et al. | |
| 4,265,227 A | 5/1981 | Ruge | |
| 4,312,357 A | 1/1982 | Andersson et al. | |
| 4,321,930 A | 3/1982 | Jobsis et al. | |
| 4,495,949 A | 1/1985 | Stoller | |
| 4,502,075 A | 2/1985 | DeForest et al. | |
| 4,567,896 A | 2/1986 | Barnea | |
| 4,576,175 A | 3/1986 | Epstein | |
| 4,619,249 A | 10/1986 | Landry | |
| 4,699,149 A | 10/1987 | Rice | |
| 4,766,299 A | 8/1988 | Tierney et al. | |
| 4,771,308 A | 9/1988 | Tejima et al. | |
| 4,780,919 A | 11/1988 | Harrison | |
| 4,817,622 A | 4/1989 | Pennypacker et al. | |
| RE33,234 E | 6/1990 | Landry | |
| 5,146,923 A | 9/1992 | Dhawan | |
| 5,214,458 A | 5/1993 | Kanai | |
| 5,261,581 A | 11/1993 | Harden | |
| 5,406,070 A | 4/1995 | Edgar et al. | |
| 5,418,546 A | 5/1995 | Nakagakiuchi et al. | |
| 5,423,091 A | 6/1995 | Lange | |
| D362,910 S | 10/1995 | Creaghan | |
| 5,504,316 A | 4/1996 | Bridgelall et al. | |
| 5,519,208 A | 5/1996 | Esparza et al. | |
| 5,541,820 A | 7/1996 | McLaughlin | |
| 5,598,842 A | 2/1997 | Ishihara et al. | |
| 5,603,328 A | 2/1997 | Zucker et al. | |
| 5,608,210 A | 3/1997 | Esparza et al. | |
| 5,610,387 A | 3/1997 | Bard et al. | |
| 5,631,976 A | 5/1997 | Bolle et al. | |
| 5,678,555 A | 10/1997 | O'Connell | |
| 5,719,399 A | 2/1998 | Alfano et al. | |
| 5,756,981 A | 5/1998 | Roustaei et al. | |
| 5,772,593 A | 6/1998 | Hakamata | |
| 5,787,185 A | 7/1998 | Clayden | |
| 5,836,877 A | 11/1998 | Zavislan | |
| 5,847,394 A | 12/1998 | Alfano et al. | |
| 5,860,967 A | 1/1999 | Zavislan et al. | |
| 5,929,443 A | 7/1999 | Alfano et al. | |
| 5,947,906 A | 9/1999 | Dawson, Jr. et al. | |
| 5,969,754 A * | 10/1999 | Zeman | 348/136 |
| 5,982,553 A | 11/1999 | Bloom et al. | |
| 5,988,817 A | 11/1999 | Mizushima et al. | |
| 5,995,856 A | 11/1999 | Manheimer et al. | |
| 6,032,070 A | 2/2000 | Flock et al. | |
| 6,056,692 A | 5/2000 | Schwartz | |
| 6,061,583 A | 5/2000 | Shihara et al. | |
| 6,135,599 A | 10/2000 | Fang | |
| 6,141,985 A | 11/2000 | Cluzeau et al. | |
| 6,142,650 A | 11/2000 | Brown et al. | |
| 6,149,644 A | 11/2000 | Xie | |
| 6,178,340 B1 * | 1/2001 | Svetliza | 600/310 |
| 6,230,046 B1 | 5/2001 | Crane et al. | |
| 6,251,073 B1 | 6/2001 | Imran et al. | |
| 6,263,227 B1 | 7/2001 | Boggett et al. | |
| 6,301,375 B1 | 10/2001 | Choi | |
| 6,314,311 B1 | 11/2001 | Williams et al. | |
| 6,334,850 B1 | 1/2002 | Amano et al. | |
| 6,424,858 B1 | 7/2002 | Williams | |
| 6,438,396 B1 | 8/2002 | Cook et al. | |
| 6,463,309 B1 | 10/2002 | Ilia | |
| 6,464,646 B1 | 10/2002 | Shalom et al. | |
| 6,542,246 B1 | 4/2003 | Toida | |
| 6,556,854 B1 | 4/2003 | Sato et al. | |
| 6,556,858 B1 | 4/2003 | Zeman | |
| 6,648,227 B2 | 11/2003 | Swartz et al. | |
| 6,650,916 B2 | 11/2003 | Cook et al. | |
| 6,689,075 B2 | 2/2004 | West | |
| 6,690,964 B2 | 2/2004 | Bieger et al. | |
| 6,702,749 B2 | 3/2004 | Paladini et al. | |
| 6,719,257 B1 | 4/2004 | Greene et al. | |
| 6,782,161 B2 | 8/2004 | Barolet et al. | |
| 6,882,875 B1 | 4/2005 | Crowley | |
| 6,889,075 B2 | 5/2005 | Marchitto et al. | |
| 6,913,202 B2 | 7/2005 | Tsikos et al. | |
| 6,923,762 B1 | 8/2005 | Creaghan | |
| 6,980,852 B2 | 12/2005 | Jersey-Wiluhn et al. | |
| 7,158,660 B2 | 1/2007 | Gee et al. | |
| 7,225,005 B2 | 5/2007 | Kaufman et al. | |
| 7,239,909 B2 | 7/2007 | Zeman | |
| 7,247,832 B2 | 7/2007 | Webb | |
| 7,283,181 B2 | 10/2007 | Allen | |
| 7,302,174 B2 | 11/2007 | Tan et al. | |
| 7,333,213 B2 | 2/2008 | Kempe | |
| D566,283 S | 4/2008 | Brafford et al. | |
| 7,359,531 B2 | 4/2008 | Endoh et al. | |
| 7,431,695 B1 | 10/2008 | Creaghan | |
| 7,532,746 B2 | 5/2009 | Marcotte et al. | |
| 7,608,057 B2 | 10/2009 | Woehr et al. | |
| 7,846,103 B2 | 12/2010 | Cannon | |
| 7,904,138 B2 | 3/2011 | Goldman et al. | |
| 7,925,332 B2 | 4/2011 | Crane et al. | |
| 8,078,263 B2 | 12/2011 | Zeman et al. | |
| 8,187,189 B2 | 5/2012 | Jung et al. | |
| 8,199,189 B2 | 6/2012 | Kagenow et al. | |
| 8,320,998 B2 | 11/2012 | Sato | |
| 8,336,839 B2 | 12/2012 | Timoszyk et al. | |
| 8,364,246 B2 | 1/2013 | Thierman | |
| 8,494,616 B2 | 7/2013 | Zeman | |
| 8,498,694 B2 | 7/2013 | McGuire, Jr. et al. | |
| 8,509,495 B2 | 8/2013 | Xu et al. | |
| 8,548,572 B2 | 10/2013 | Crane et al. | |
| 8,649,848 B2 | 2/2014 | Crane et al. | |
| 8,818,493 B2 * | 8/2014 | Goldman et al. | 600/473 |
| 2002/0016533 A1 | 2/2002 | Marchitto | |
| 2002/0118338 A1 | 8/2002 | Kohayakawa | |
| 2003/0018271 A1 | 1/2003 | Kimble | |
| 2003/0125629 A1 | 7/2003 | Ustuner | |
| 2004/0015158 A1 | 1/2004 | Chen et al. | |
| 2004/0022421 A1 | 2/2004 | Endoh et al. | |
| 2004/0046031 A1 | 3/2004 | Knowles et al. | |
| 2004/0171923 A1 | 9/2004 | Kalafut et al. | |
| 2004/0222301 A1 | 11/2004 | Willins et al. | |
| 2005/0017924 A1 | 1/2005 | Utt et al. | |
| 2005/0043596 A1 | 2/2005 | Chance | |
| 2005/0047134 A1 | 3/2005 | Mueller et al. | |
| 2005/0113650 A1 | 5/2005 | Pacione et al. | |
| 2005/0131291 A1 | 6/2005 | Floyd et al. | |
| 2005/0135102 A1 | 6/2005 | Gardiner et al. | |
| 2005/0141069 A1 | 6/2005 | Wood et al. | |
| 2005/0143662 A1 | 6/2005 | Marchitto et al. | |
| 2005/0146765 A1 | 7/2005 | Turner | |
| 2005/0157939 A1 | 7/2005 | Arsenault et al. | |
| 2005/0161051 A1 | 7/2005 | Pankratov et al. | |
| 2005/0168980 A1 | 8/2005 | Dryden et al. | |
| 2005/0174777 A1 | 8/2005 | Cooper et al. | |
| 2005/0175048 A1 | 8/2005 | Stern et al. | |
| 2005/0215875 A1 | 9/2005 | Khou | |
| 2005/0281445 A1 | 12/2005 | Marcotte et al. | |
| 2006/0020212 A1 | 1/2006 | Xu | |
| 2006/0025679 A1 | 2/2006 | Viswanathan et al. | |
| 2006/0081252 A1 | 4/2006 | Wood | |
| 2006/0103811 A1 | 5/2006 | May et al. | |
| 2006/0122515 A1 | 6/2006 | Zeman | |
| 2006/0129037 A1 | 6/2006 | Kaufman et al. | |
| 2006/0129038 A1 | 6/2006 | Zelenchuk et al. | |
| 2006/0173351 A1 | 8/2006 | Marcotte et al. | |
| 2006/0184040 A1 | 8/2006 | Keller et al. | |

(56) References Cited

U.S. PATENT DOCUMENTS

| | | |
|---|---|---|
| 2006/0232660 A1 | 10/2006 | Nakajima et al. |
| 2006/0253010 A1 | 11/2006 | Brady et al. |
| 2006/0271028 A1 | 11/2006 | Altshuler et al. |
| 2007/0016079 A1 | 1/2007 | Freeman et al. |
| 2007/0115435 A1 | 5/2007 | Rosendaal |
| 2008/0045841 A1 | 2/2008 | Wood et al. |
| 2008/0147147 A1 | 6/2008 | Griffiths et al. |
| 2008/0194930 A1 | 8/2008 | Harris et al. |
| 2010/0051808 A1 | 3/2010 | Zeman et al. |
| 2010/0061598 A1 | 3/2010 | Seo |
| 2010/0087787 A1 | 4/2010 | Woehr et al. |
| 2010/0177184 A1 | 7/2010 | Berryhill et al. |
| 2010/0312120 A1 | 12/2010 | Meier |
| 2014/0039309 A1 | 2/2014 | Harris et al. |
| 2014/0046291 A1 | 2/2014 | Harris et al. |

FOREIGN PATENT DOCUMENTS

| | | |
|---|---|---|
| GB | 1507329 | 4/1978 |
| JP | 08023501 A | 1/1996 |
| JP | 2002 328428 A | 11/2002 |
| JP | 2003-6542246 B1 | 4/2003 |
| JP | 2003-6556854 B1 | 4/2003 |
| JP | 2004 237051 | 8/2004 |
| KR | 2003/0020152 A | 3/2003 |
| WO | WO 94 22370 | 10/1994 |
| WO | WO 96 39926 | 12/1996 |
| WO | WO 9826583 | 6/1998 |
| WO | WO 01 82786 | 11/2001 |
| WO | WO 03 009750 | 2/2003 |
| WO | WO 2007 078447 | 12/2007 |

OTHER PUBLICATIONS

Nikbin, Darius, "IPMS Targets Colour Laser Projectors," Optics & Laser Europe, Mar. 2006, Issue 137, p. 11.

http://sciencegeekgirl.wordpress. com/category/science-myths/page/2/ Myth 7: Blood is Blue, (Jun. 7, 2008).

http://www.exploratorium.edu/sports/hnds_up/hands6.html "Hands Up! To Do & Notice: Getting the Feel of Your Hand", (as early as Jul. 23, 1997).

http://www.wikihow.com/See-Blood-Veins-in-Your-Hand-With-a-Flashlight "How to See Blood Veins in Your Hand With a Flashlight" Mar. 29, 2007.

* cited by examiner

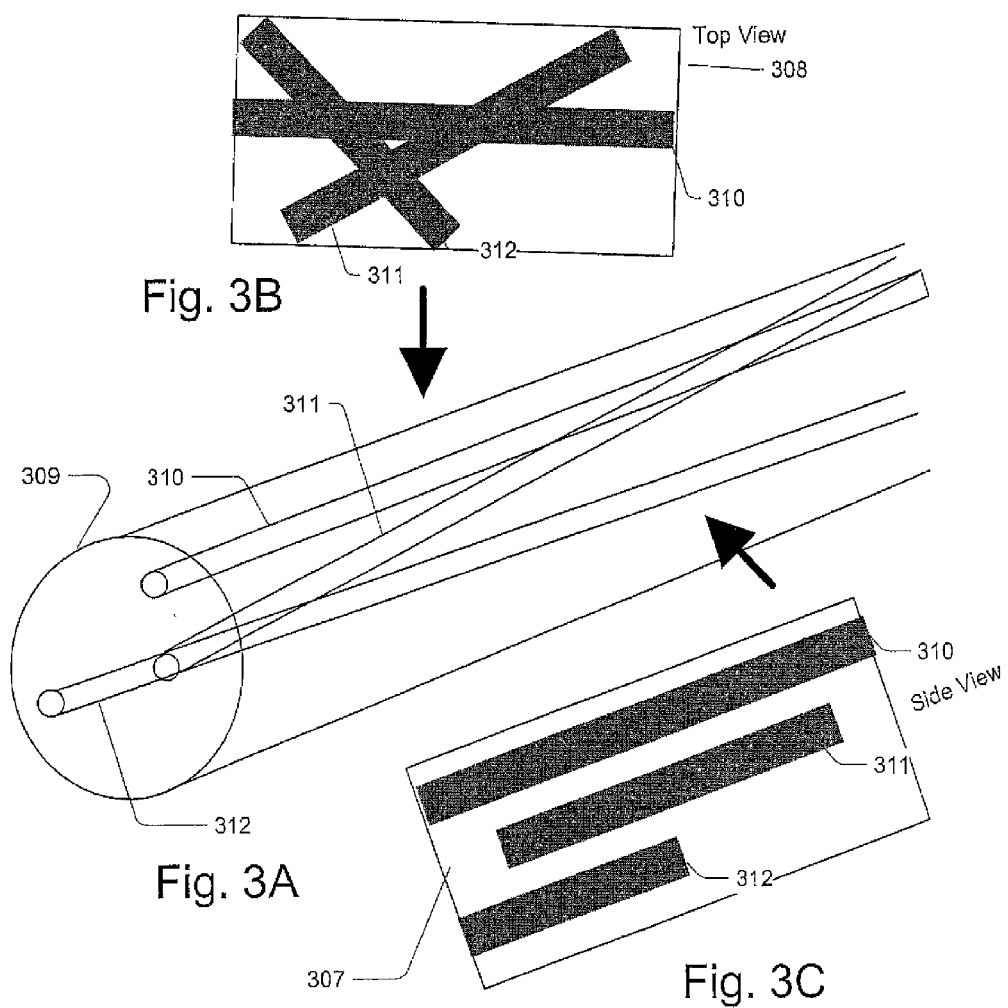

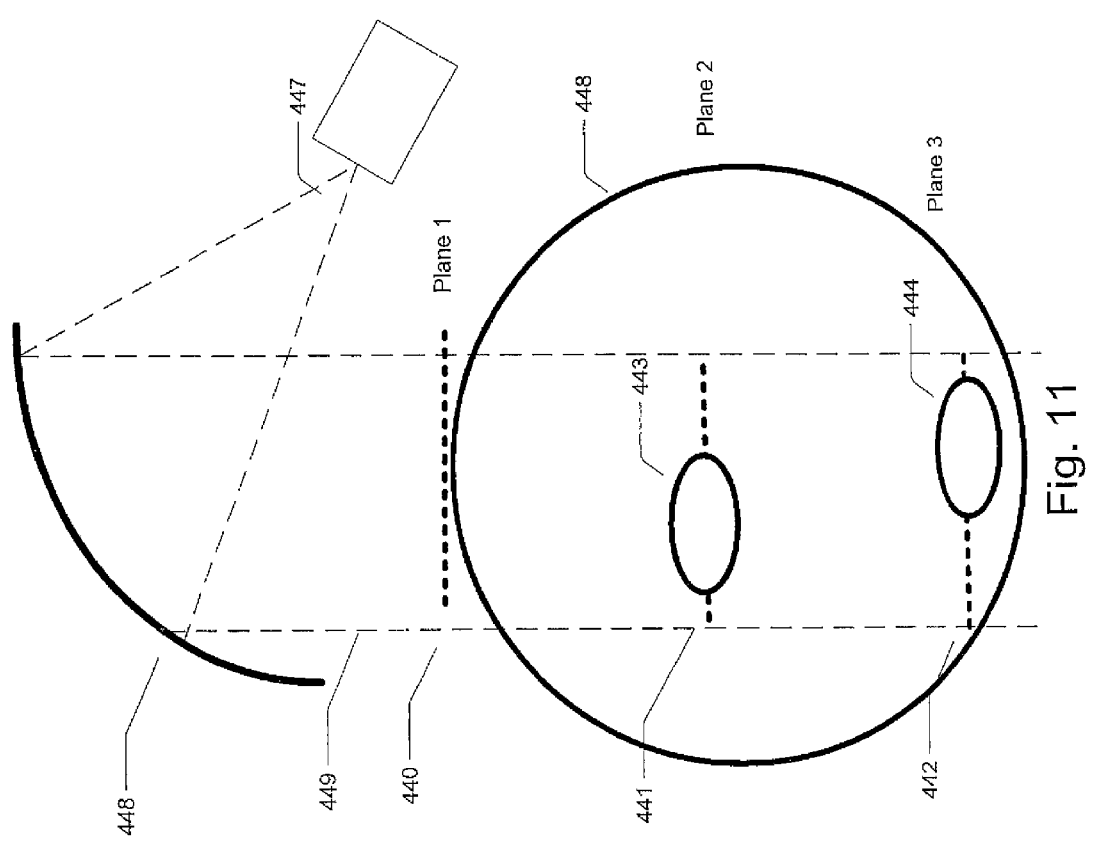

THREE DIMENSIONAL IMAGING OF VEINS

This application is a continuation of U.S. application Ser. No. 13/135,591, filed on Jan. 25, 2011, now issued as U.S. Pat. No. 8,818,493, which is a continuation of U.S. application Ser. No. 11/823,862, filed Jun. 29, 2006, now issued as U.S. Pat. No. 7,983,738, which claims priority on U.S. Provisional Patent Application Ser. No. 60/817,623 filed on Jun. 29, 2006 the disclosures of which are incorporated herein by reference. This application is also a continuation in part of U.S. application Ser. No. 11/478,322 also filed Jun. 29, 2006, now issued as U.S. Pat. No. 8,478,386, which claims priority on U.S. Provisional Patent Application Ser. No. 60/757,704, entitled "Micro Vein Enhancer" filed on Jan. 10, 2006, the disclosures of which are also incorporated by reference herein.

SUMMARY OF THE INVENTION

A laser based imaging system that can image veins, arteries, or other organs containing blood, and can generate three dimensional images representative thereof.

BACKGROUND OF THE INVENTION

It is known in the art to use an apparatus to enhance the visual appearance of the veins and arteries in a patient to facilitate insertion of needles into those veins and arteries as well as other medical practices that require the identification of vein and artery locations. Such a system is described in U.S. Pat. Nos. 5,969,754 and 6,556,858 incorporated herein by reference as well as publication entitled "The Clinical Evaluation of Vein Contrast Enhancement". Luminetx is currently marketing such a device under the name "Veinviewer Imaging System" and information related thereto is available on their website, which is incorporated herein by reference.

The Luminetx Vein Contrast Enhancer (hereinafter referred to as LVCE) utilizes a light source for flooding the region to be enhanced with near infrared light generated by an array of LEDs. A CCD imager is then used to capture an image of the infrared light reflected off the patient. The resulting captured image is then projected by a visible light projector onto the patient in a position closely aligned with the image capture system. The light source for flooding the region to be enhanced does not deeply penetrate into the patient, and therefore, only the veins on the surface of the patient are imaged. Further, the image representative of the veins which is rendered onto the patient is two dimensional and does not provide any depth information. Still further, there is no method using such technology to display blood flowing at a given depth in the patient.

BRIEF DESCRIPTION OF THE DRAWINGS

FIG. 3A is a side cutaway view of a patient's arm, illustrating the veins within the patient's arm.

FIG. 3B is a top view of the veins in the arm of the patient in FIG. 3A.

FIG. 3C is a side view of the veins in the arm of the patient in FIG. 3A.

FIG. 11 is an illustration of how an embodiment of the laser based vein enhancer of the present invention accurately projects the correct vein size regardless of the depth of the veins within the patient's arm.

DETAILED DESCRIPTION OF THE INVENTION

Preliminary application No. 60/757,704, incorporated herein by reference, described a miniature laser based system for imaging a patient's veins and arteries and then rendering them onto the surface of the patient's skin. Tests of such a system has shown that the laser based imaging system can penetrate and image very deeply into the patients body, and in some cases, such as the hand or arm, can image entirely through the hand or arm. Further, it has been found that the depth of penetration of the imaging is a function of the amount of laser power applied. Using these principals, a three dimensional imaging system is now described.

Figure 1:
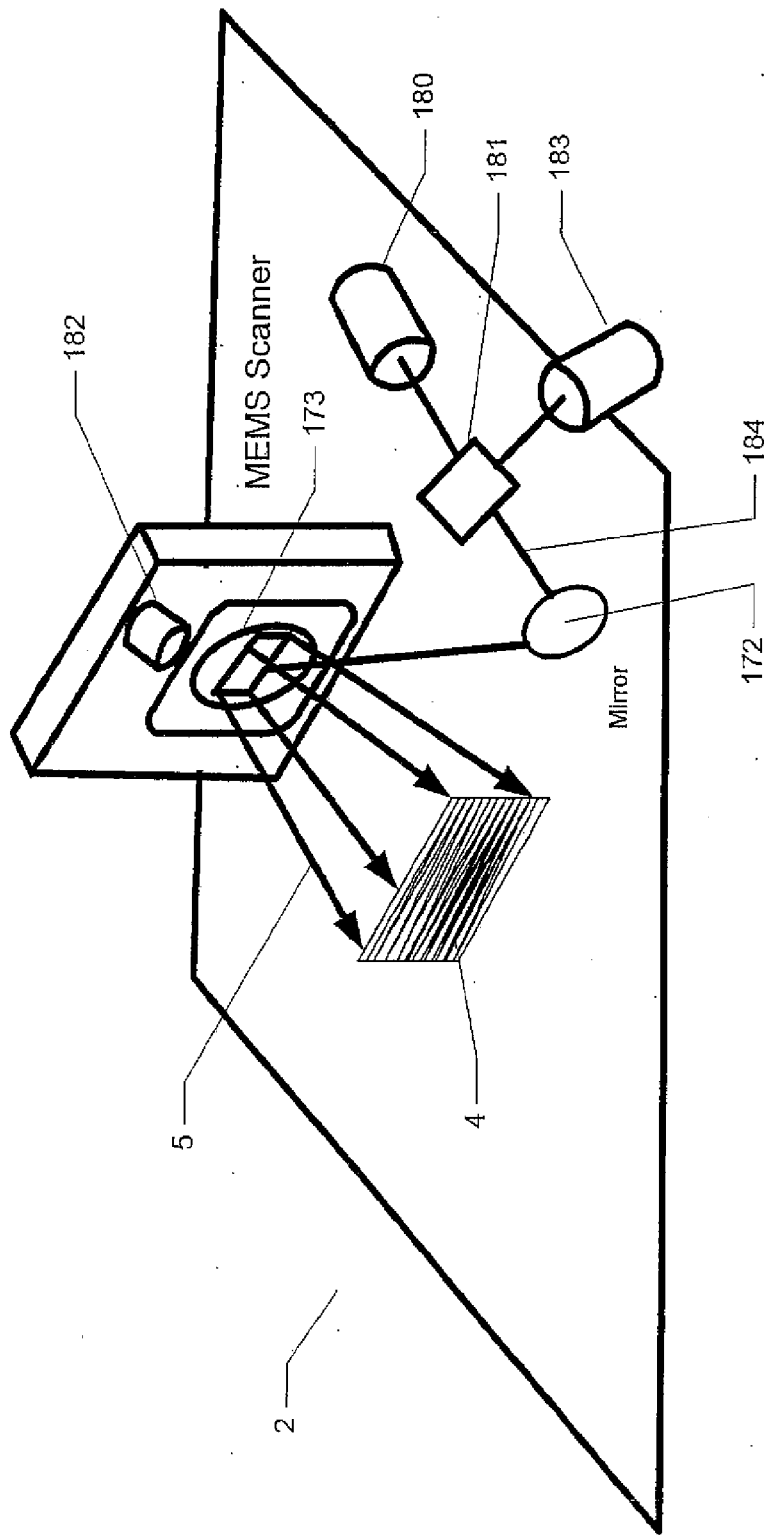
FIG. 1 shows a perspective view of the optical apparatus for the laser based vein enhancer of the present invention.

FIG. 1. shows the optical apparatus for a laser based vein enhancer. A single colored laser 180, for example a 630 nm semiconductor red laser, is projected into combiner 181. A semiconductor laser 183 is also projected into the combiner 181. Laser 183 may have a wavelength from 700 nm to 1000 nm, with a preferred wavelength of 740 nm. An illustrative example of a semiconductor 740 nm laser is Sacher Lasertechnik's Fabry Perot Diode Laser 740 nm, 10 mw, model number FP-0740-10. The combiner 181 outputs a combined laser beam 184 which is the combination of the 630 nm red and the 740 nm laser beams. Combiners for combining two lasers of different frequencies are well known in the art and will not be further described herein. The combined laser beam 184 is positioned to hit off mirror 172 and then to hit the MEMS scanner 173. The MEMS scanner moves in a raster pattern thereby causing the combined laser beam to move along optical path 5 forming a raster pattern at the field of view 4. A photodetector 182 which is responsive to the 740 nm wavelength is provided and receives 740 nm light reflected off objects in the field of view. The photodetector 182 outputs an analog signal representing the amount of 740 nm light received. An illustrative example of a photodetector is Roithner Lasertechnik's model number EPD-740-1.

Figure 2:
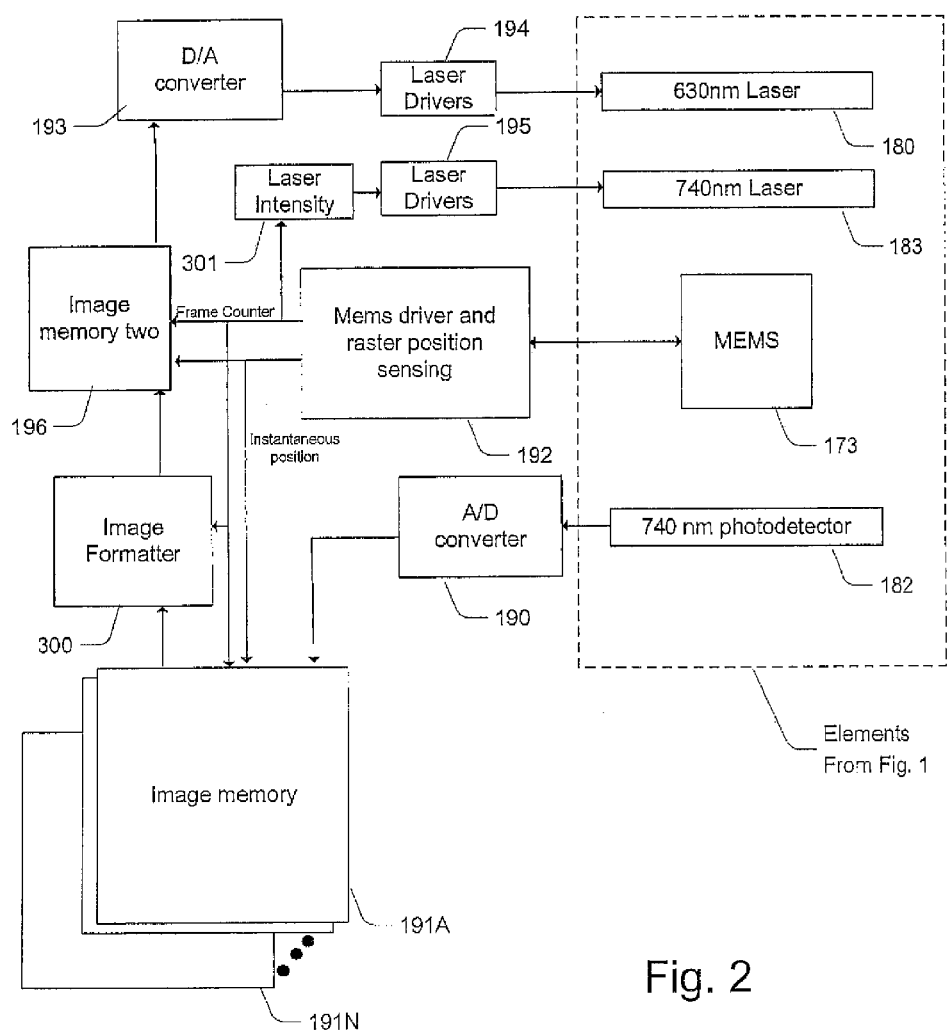
FIG. 2 is a control block diagram of the controlling elements of the optical apparatus of FIG. 1.

FIG. 2 shows a control block diagram for controlling the elements in FIG. 1 to form a three dimensional imaging system. An electronic block 192 for driving the MEMS driver and for sensing the position of the raster scanner is provided. This block 192 generates the signals required to drive the MEMS scanner 173 in a raster pattern, and also determines the exact instantaneous location of the MEMS scanner and communicates this information to an image memory array 191A-191N. This electronic block 192 also generates output signals indicating the frame count and communicates such signals to image memory array 191A-191N, image formatter 300, image memory two 196, and laser intensity block 301.

Assuming the frame rate is sixty frames per second, the frame count will cycle from one through sixty. The operation is as follows. The MEMS scanner 173 is driven in a raster pattern. The first full frame after achieving a stable raster pattern will be identified as frame one by the frame counter. Thereafter each subsequent frame will increase the frame counter by one, up to sixty, and thereafter the frame counter will reset to one and then start the cycle again. Laser intensity block 301 drives the laser drivers 195 at a select one of sixty levels depending upon the current frame counter level. More particularly, the laser intensity block 301 drives the laser drivers 195 in such a manner that the power output from the 740 nm laser 183 linearly increases in sixty steps as the frame counter increments from one to sixty. During the first sixty frames of operation the laser drive 194 for the 630 nm laser 180 is turned off. The light from the 740 nm 183 is reflected off the patient and absorbed by the blood in the veins in a patient's body and the reflected light is sensed and converted into an analog signal by 740 nm photo detector 182. The analog signal is then passed through an A/C converter 190 which outputs a digital representation to image memory 191A-191N, wherein in this example A=1 and N=60. Image memory 191A-191N receives instantaneous position information from the electronic block 192, and based upon such information, the digital representation for each pixel is stored in a memory location corresponding to a particular pixel. This is repeated for each pixel within a frame. In this manner, each frame is stored in an associated image memory. Upon completion of the first sixty frames, the image memory 191A-191N contains sixty images of the veins within the field of view of the 740 nm laser 183, wherein each sequential image memory contains an image which has been obtained with increased laser intensity. After the completion of the sixtieth frame, the image memory is forwarded to an image formatter 300, which in turn forms an image which is transferred to image memory two 196. During each of the next sixty frames of the cycle, the data in the image memory two 196 is read out as a function of the instantaneous position information provided by the electronic block 192 and provided to a D/A converter 193 which outputs an analog signal to laser drive 194 which drives the 630 nm laser 180. In this manner, the image that was stored in image memory two 196 is projected by the 630 nm laser 180 onto the patient. In this manner, the veins that are in the field of view become visible to the practitioner.

While in the above embodiment, the frame count (number of slices of images taken) was sixty, the frame count could be more or less than sixty. Also, the laser intensity 301 was indicated to go up linearly. It is also possible to have a look-up table or algorithm which provides for non-linear step-ups in power. To simplify the discussion, the power changes have been described in a "step-up" fashion. The order in which the various steps are taken are unimportant, it is the capture of the vein signal at various intensities is what is important to the process.

The operation of image formatter 300 will now be described in greater detail. To simplify the Figs. shown, a maximum frame count of 17 (N=17) is illustrated as opposed to the frame rate of 60 (N=60) previously described. Accordingly, for the purpose of the illustrations the laser will cycle through 17 frames at 17 different increasing power levels. Referring to FIG. 3A, a three dimension illustration of a patient's arm 309 is shown. The arm has a top vein 310 which is closest to the top surface and bottom vein 312 which is the deepest as viewed from the top surface and middle vein 311 which is between the two. FIG. 3B shows a top view 308 of the veins 310, 311 and 312 as viewed from the top of the arm if the arm was transparent and the veins were not. FIG. 3C shows a side view 307 of the veins 310, 311 and 312 as viewed from the side of the arm (assuming again for the moment the arm is transparent and the veins are not).

Figure 4A:
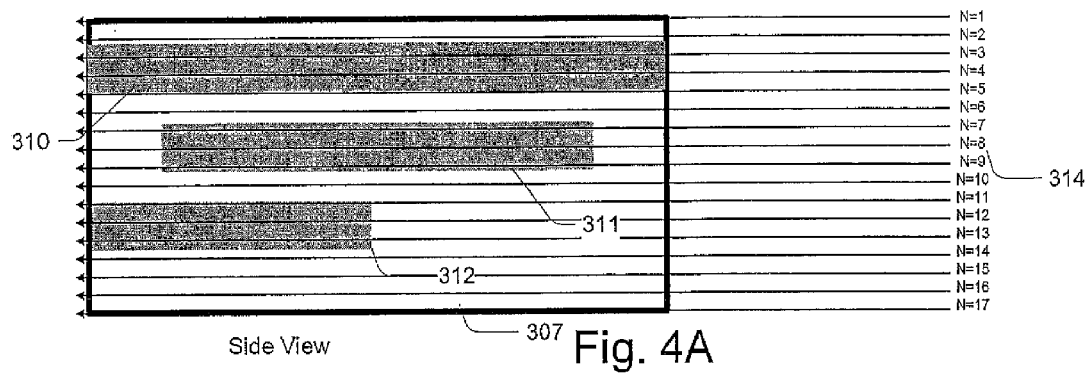
FIG. 4A is a side view of the veins in the arm of the patient in FIG. 3A, showing the scan depth lines from N=1 through N=17.
Figure 4B:
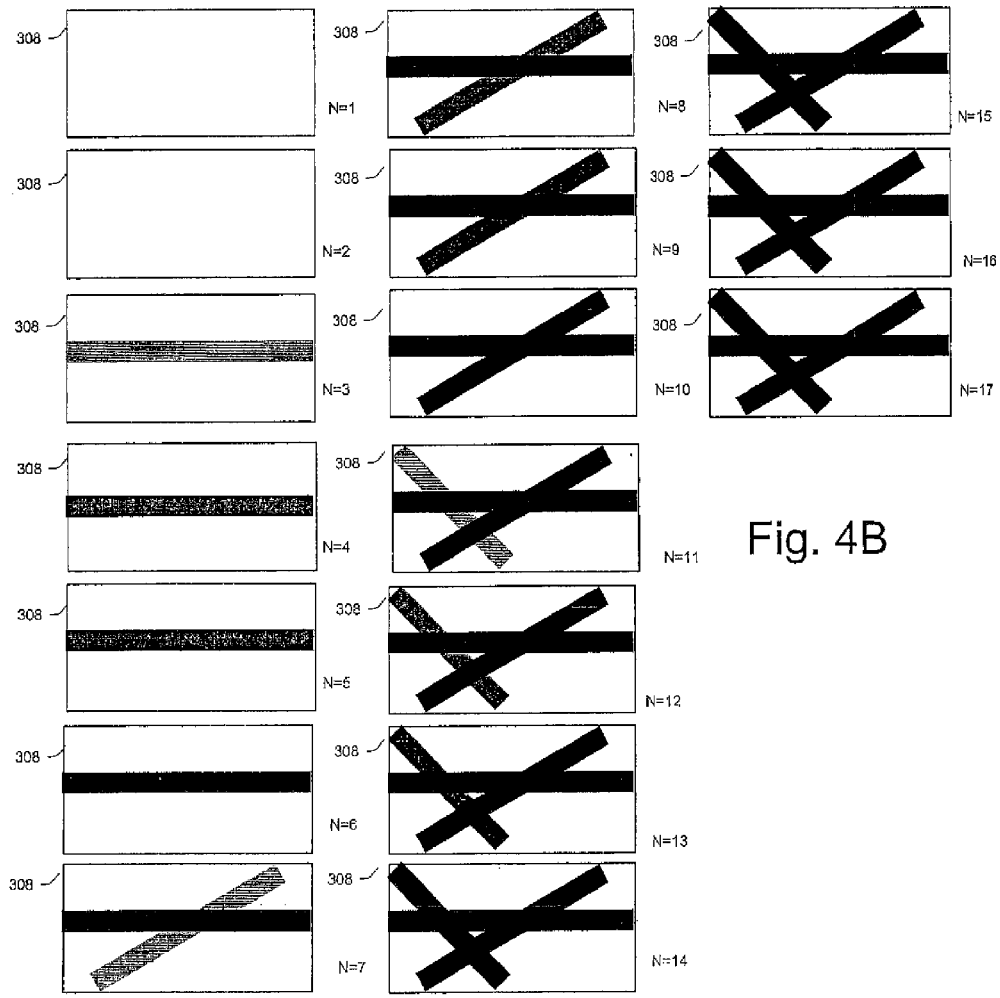
FIG. 4B shows 17 images for N=1 through N=17 of the arm of the patient in FIG. 3A that are stored in the image memory of laser based vein enhancer of the present invention.

The laser based vein enhancer of FIG. 1 and FIG. 2 is positioned so that the field of view corresponds with the top view 308 of the patient's arm 309 shown in FIG. 3. FIG. 4A again shows the side view 307 but also includes along the right edge scan depth lines 314 N=1 through N=17. These scan depth lines 314 indicate how deeply the laser light penetrates into the arm at each respective laser intensity level N=1 through N=17. FIG. 4B shows 0.17 images N=1 through N=17 that are stored in image memory 191A-191N. Referring to the image memory associated with frame one (N=1), the intensity of the laser only penetrates the patient arm to the depth shown by the N=1 scan depth line 314. Since this depth does not reach vein 310, 311 or 312 as shown in FIG. 4A, the image stored for the first frame N=1 is blank. The same applies to the second frame N=2. The third frame N=3 reaches partly into vein 310 and accordingly the image stored in image memory associated with the third frame (where N=3) begins to faintly show vein 310. Frames 4, 5 and 6 each penetrate successively deeper into vein 310 and therefore the image of vein 310 gets successively darker in the image memory 191A-191N associated with frames 4, 5 and 6 (N=3, 4 and 5). Similarly, starting with frame 7 (N=7), the middle vein 311 begins to appear and then starting with frame 11 (N=11) the deepest vein 312 begins to appear. By frame 14 the laser light penetrates all the way through veins 310, 311, and 312 and therefore the images for frames 14 through frame 17 are approximately the same and show all the veins.

If the image for frame 17 (N=17) were to be projected onto the patients arm, there would be no way for the practitioner to determine the relative depths of veins 310, 311 or 312. Accordingly the image needs to be reformatted so as to provide additional information to the practitioner before projecting on the patients arm.

Figure 5:
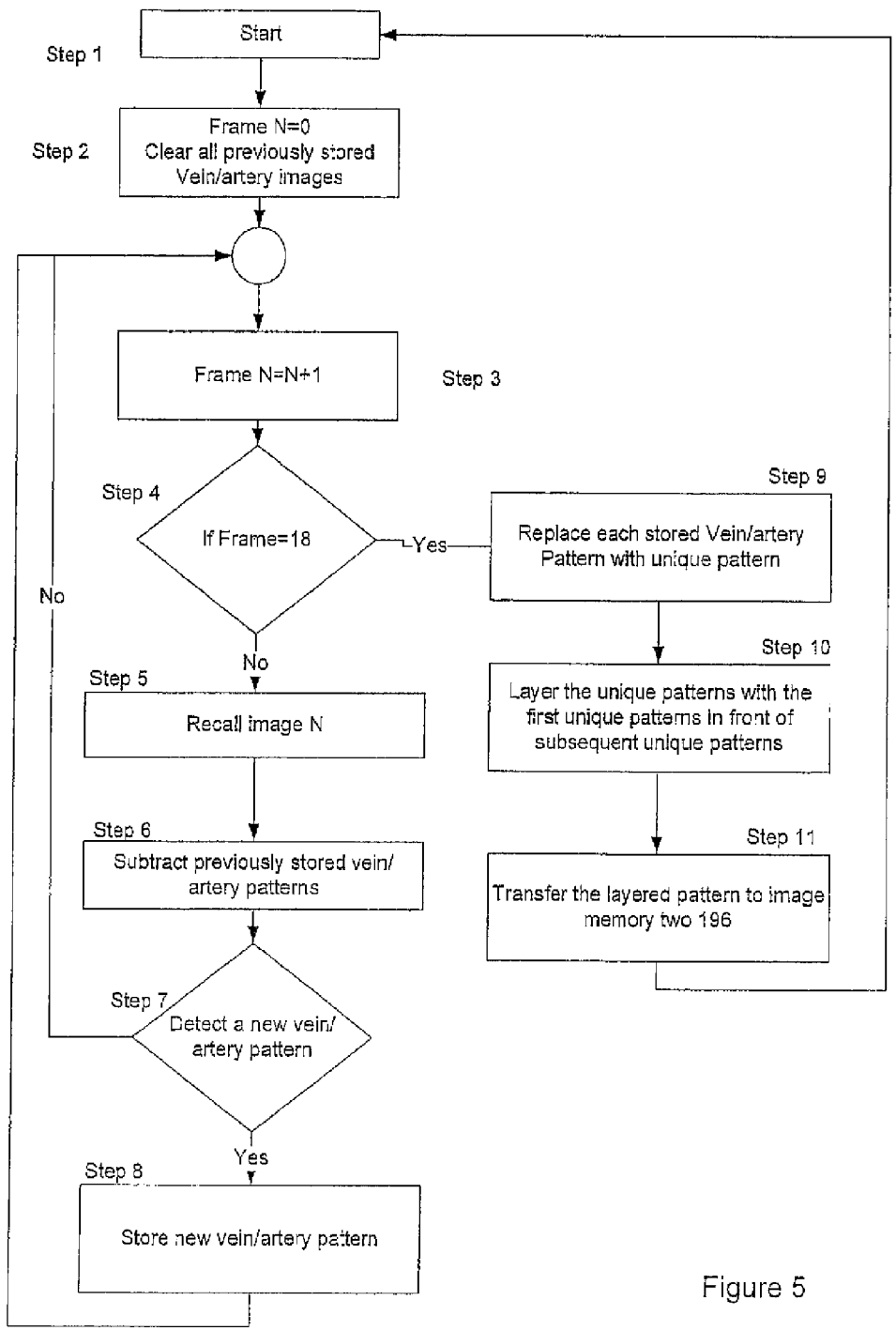
FIG. 5 is a flow chart illustrating an embodiment of the image formatter of the optical apparatus of FIG. 2.

Referring to FIG. 5, an illustrative embodiment of the image formatter 300 of FIG. 2 is flow-charted. The frame counter N is set at 0 in step 2 and all previously stored vein/artery images are cleared. In step 3 the counter N is increased by one. In step 4 the frame counter is tested to see if all 17 frames are completed. Accordingly, step 5 will be reached for each of the 17 successive images (N=1 through N=17). In step 5 the image N is recalled from the appropriate image memory 191A-191N. In step 6 all previously stored vein/artery pattern are subtracted. During the first frame N=1 there will be no previously stored vein/artery pattern to be subtracted since they were cleared at step 2. At step 7, image processing is performed to detect whether a vein or artery pattern is found. Since it is know that veins and arteries are tube shaped and have a length much greater than their diameter, relative straightforward computer processing can be used to identify such a pattern. If a new pattern is detected at step 8 the new vein/artery pattern is stored at step 9 and the program returns to step 3. If there is no new pattern detected in step 8 the program returns to step 3.

Now applying step 1 through step 8 to the images shown in FIG. 4B, assuming that image N=3 represents the first time step 7 detects a vein 310, the image of the vein 310 is stored at step 8. Thereafter, in each subsequent image processed, the image of vein 310 is removed from the image at step 6. Then assuming when the N=7 the second vein 311 is detected in step 9, the image of vein 311 is stored and accordingly removed the next time the program reaches step 6. Finally when the N=11 the deepest vein 312 is detected in step 9, the image of vein 312 is stored and accordingly removed the next time the program reaches step 6. After completing the last frame 17, the program moves to Step 9 wherein each stored vein/artery pattern is replaced with a unique pattern. For example, the pattern of vein 310 can be replaced with a diagonally striped pattern, the pattern of vein 311 can be replaced by a checked pattern, and the pattern of vein 312 can be replaced with a light grey pattern. At step 10 each of the now unique patterns for each of the stored vein/artery patterns are layered on top of each other, with the first found pattern falling on the top, the second pattern in the middle and the third pattern on the bottom. In step 11, the image of step 10 is transferred to image memory two 196 (See FIG. 2). The image of step 10 is then projected by the visible laser onto the patients arm.

Figure 6:
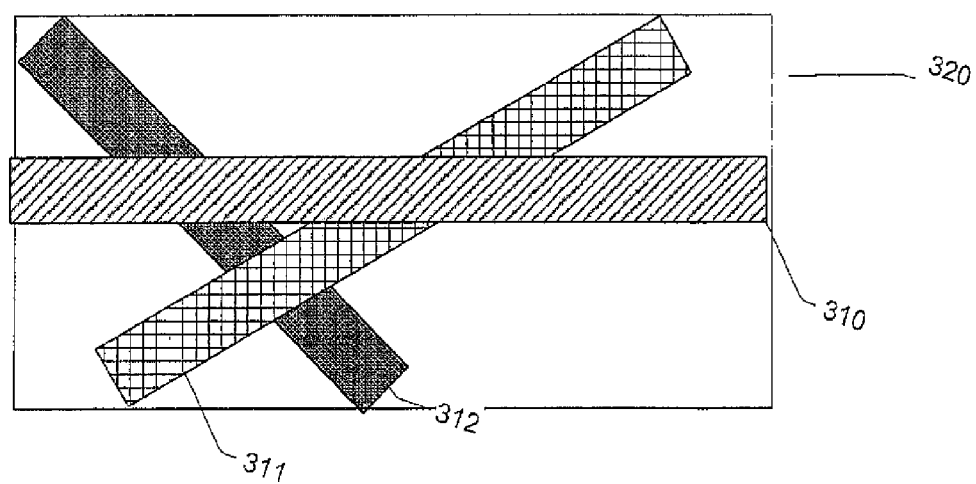
FIG. 6 is a top view of the veins in the arm of the patient in FIG. 3A, utilizing different patterns to differentiate between the various different veins and arteries.

FIG. 6 shows the resulting image 320 projected onto the patients arm. As can be seen, vein 310 is represented by the diagonally striped pattern, vein 311 represented by the checked pattern, and vein 312 by a light grey pattern. It is clear to the practitioner that vein 310 is positioned above veins 311 and 312 since the diagonally striped pattern at the intersection points of the respective veins. Similarly it is clear that vein 311 is positioned above vein 312 since the checked pattern appears at the intersection point of veins 311 and 312.

In FIG. 6, diagonal striped patterns, checked pattern, and a light grey pattern were utilized for differentiating between the various different veins/arteries, however, the invention is not limited thereto. Varying patterns, such as dotted lines having different dot-space characteristics could have been utilized to represent veins at different depths. Alternatively, solid images having different intensities could have been utilized, wherein, for example, those veins closer to the surface are represented by dark projections and deeper veins by lighter projections. Still further, the red laser 180 could be replaced by multiple color lasers, for example red, green and blue, all arranged so that their projections are aligned coaxially. By mixing the amount of each laser, color images can be projected. Accordingly, each different depth vein can be represented by a different color.

Figure 7:
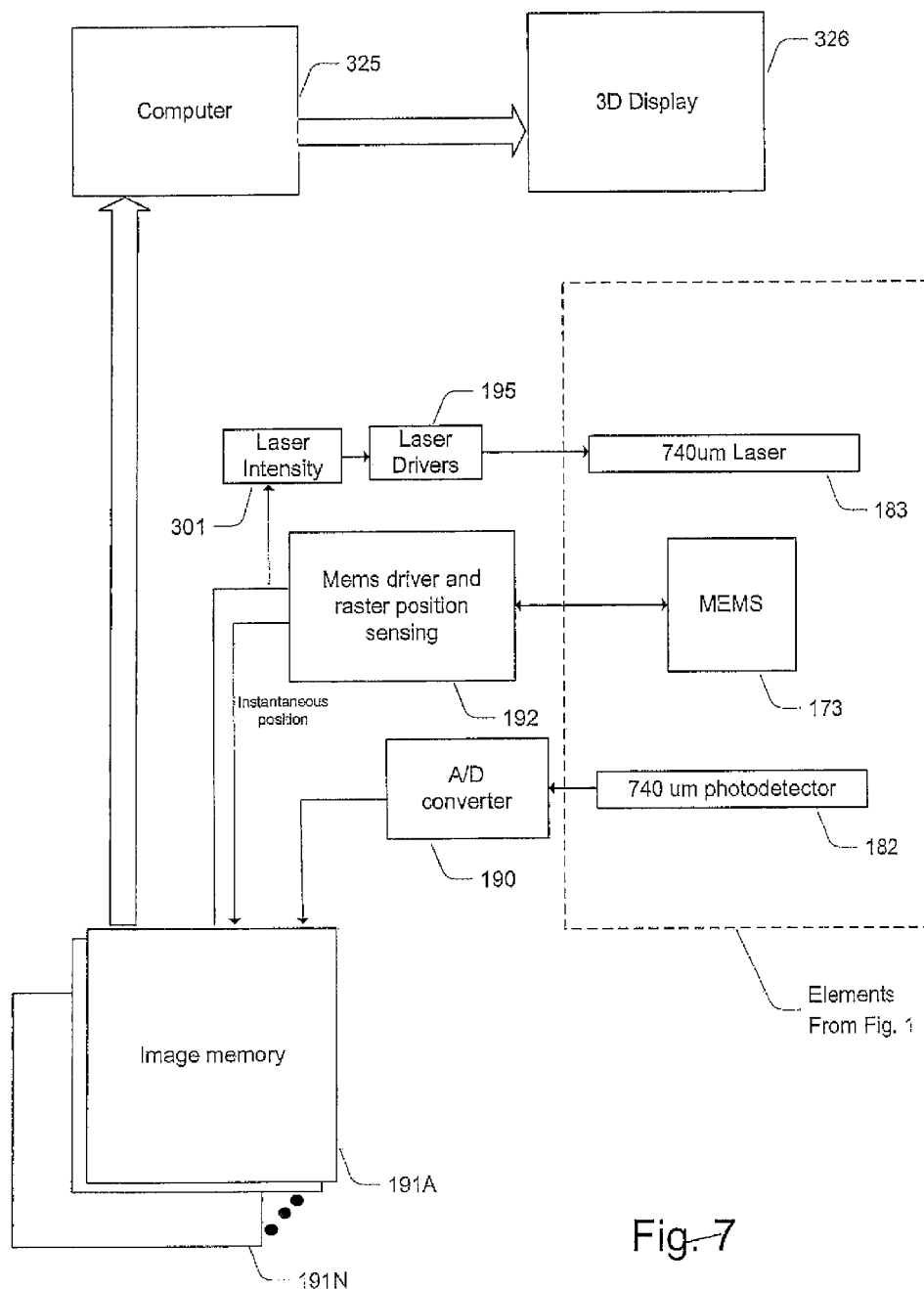
FIG. 7 is a flow chart of another embodiment of the image formatter of the optical apparatus of FIG. 2.

A further embodiment is shown with reference to FIG. 7. In this embodiment, the capturing of the vein/artery image is the same as shown previously with reference to FIG. 2 and the resulting image gets stored in image memory 191A-191N. However, in this embodiment, the image is not transmitted back onto the patient, but instead is transfer to a computer 325 and is then displayed on a three dimension (3D) display 326. More specifically, three dimensional computer software is known in the art, such a CAD (computer aid design) software or medical imaging software, for manipulating and outputting 3D images. One example of such CAD software is Solid-Works. An example of medical imaging software is an Advanced 3D Visualization and Volume Modeling software from Amira. SeeReal Technologies provides a stereo 3D display (Model C-s Display) which receives image information over a DVI connection from a graphics card of a Windows based computer and allows the user to view such 3D image without necessitating special glasses. Such Windows based computer must be fitted with a special graphics card, such as NVidea Open GL Video card, to enable the driving of the display.

Utilizing the computer 325 and 3D display 326, the practitioner can view the veins in 3 dimensions. The 3 dimensional images can be rotated by the CAD software, and cross-section slices of the 3 dimensional images can be performed.

Still further, it is possible to utilize a 2 dimensional display with CAD software converting the 3D image into meaningful 2D displays.

Figure 8:
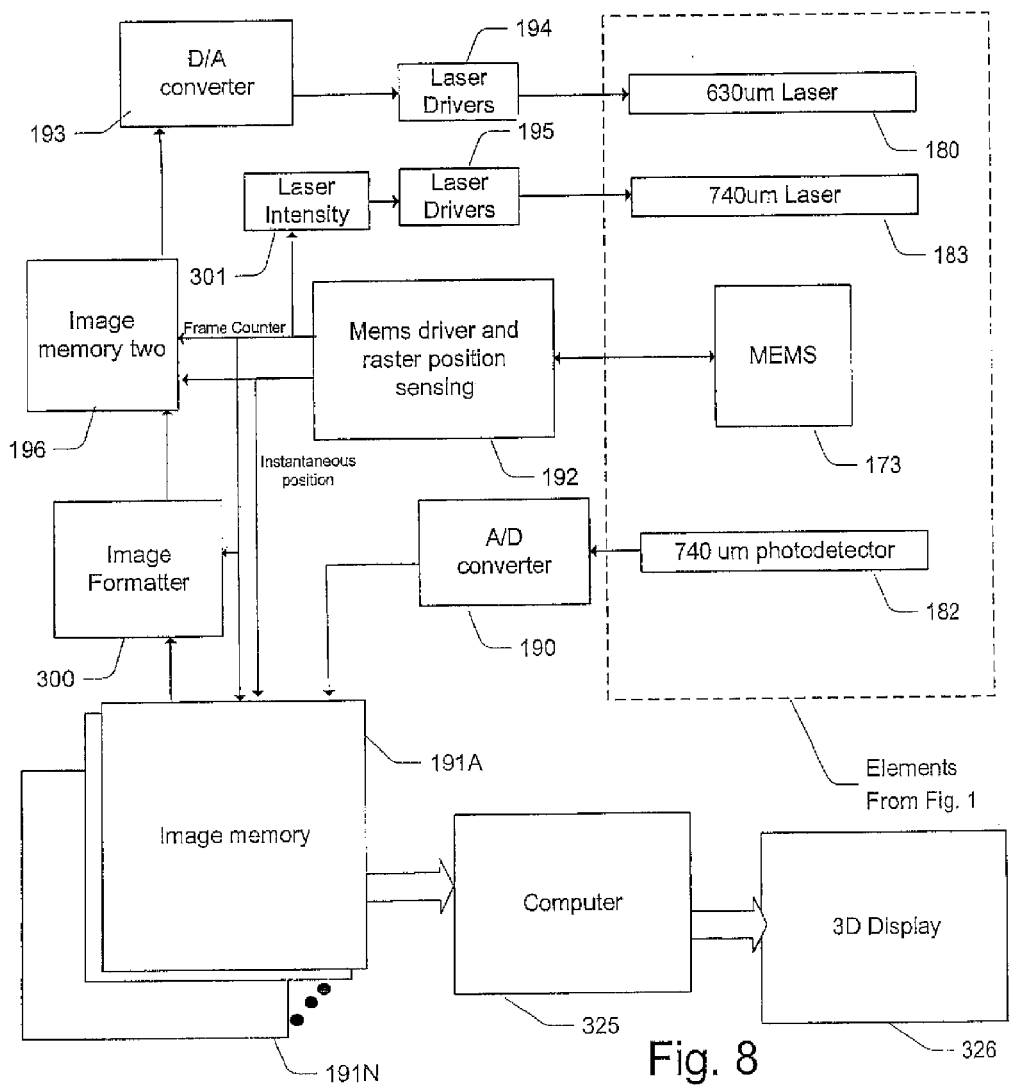
FIG. 8 is a flow chart of a third embodiment of the image formatter of the optical apparatus of FIG. 2.

FIG. 8 shows a still further embodiment wherein the visible laser projection onto the patient of FIG. 2 is combined with the 3D display 326 described with reference to FIG. 7. In this case, the image is projected onto the patient by the 630 nm laser 180 while concurrently being displayed in 3D on screen 326. In this manner the practitioner can find the exact positioning of the veins as projected on the patient and can also view a 3D representation of the veins/arteries under the surface.

Figure 9:
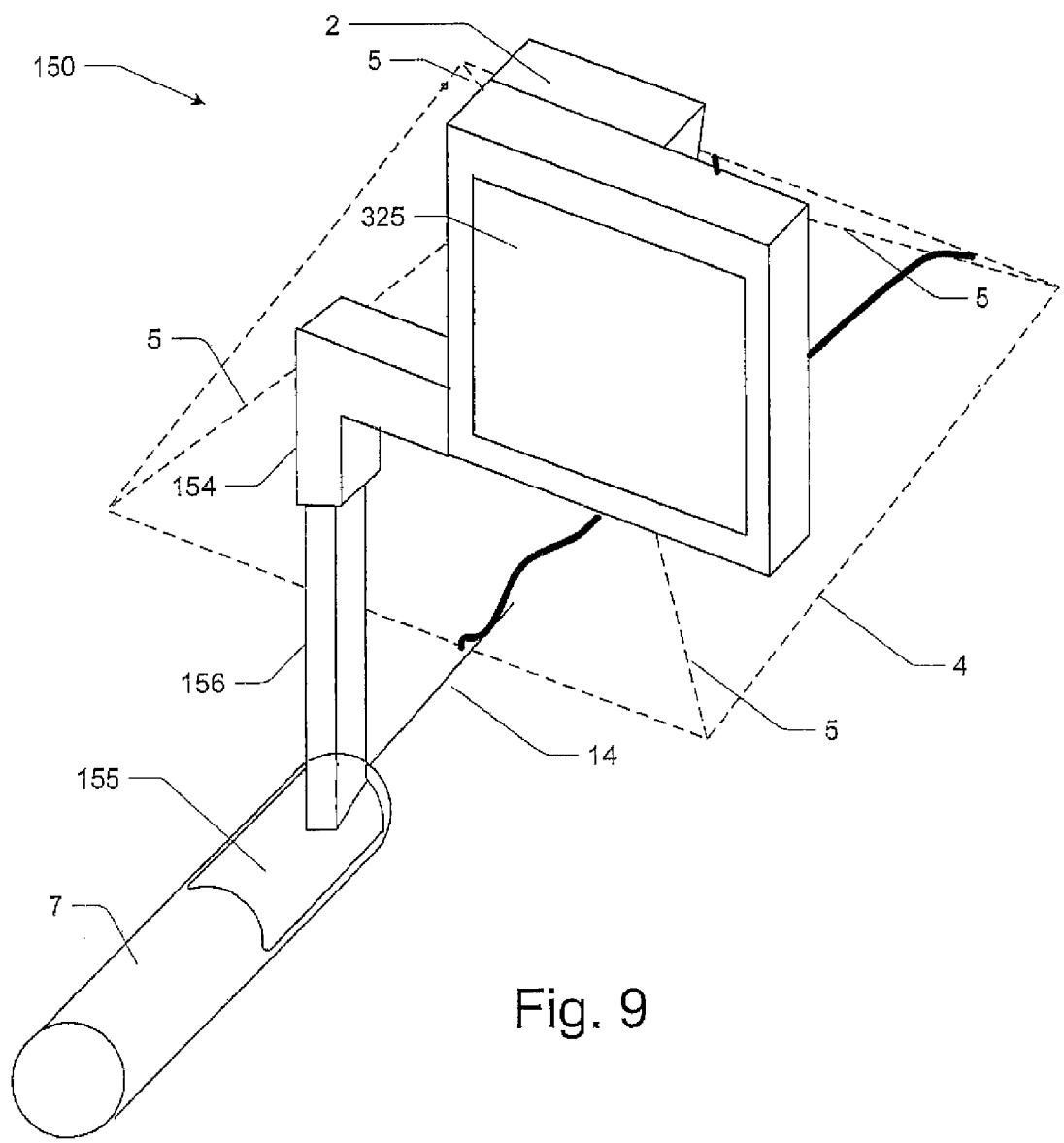
FIG. 9 shows a top front perspective view of an embodiment of the image formatter of the optical apparatus of FIG. 2.

FIG. 9 shows an embodiment similar to that shown in FIG. 15A of preliminary application No. 60/757,704.

In this embodiment the Miniature Vein Enhancer (MVE) 150 includes a small display 325, having attached thereto an attachment piece 154 and a Miniature Projection Head (MPH) 2. Although the attachment is shown at a right angle to the stem extending vertically from the vial, the stem can be at an angle to the vial and the display angle can vary, as well. A needle protector 156, connects to a vial holder 7. The attachment piece 154 receives the top of the needle protector and temporarily locks the MVE to the needle protector 156 which in turn attaches to the vial holder 7. The MPH 2 is attached to the small display 151 and is oriented so that the optical path 5 is such that the field of view 4 covers the point of the needle 14. The MPH 2 outputs the image of the veins 11 onto the field of view 4 on the patient (not shown). The MPH 2 also provides the image signal to the display 151 to be viewed on the display 151. The image signal includes both the veins and the needle 14. The display 151 includes image processing capabilities that detects the position of the tip of the needle and displays a predetermined number of pixels of the image around the tip of the needle on the display. In FIG. 14C, both the image of the needle 153 and the image of the vein 152 are shown.

The unit of FIG. 9 is driven by the electronics (not shown) describe previously in FIG. 8, wherein the computer 325, including the graphics card logic and 3D software, are miniaturized and housed in the MVE 150 and wherein the display is a small 3D display 326 attached to the MVE 150. Accordingly, when this device is used, the practitioner can view the projected image on patient, as well as the three dimensional image on the 3D display 326.

Figure 10:
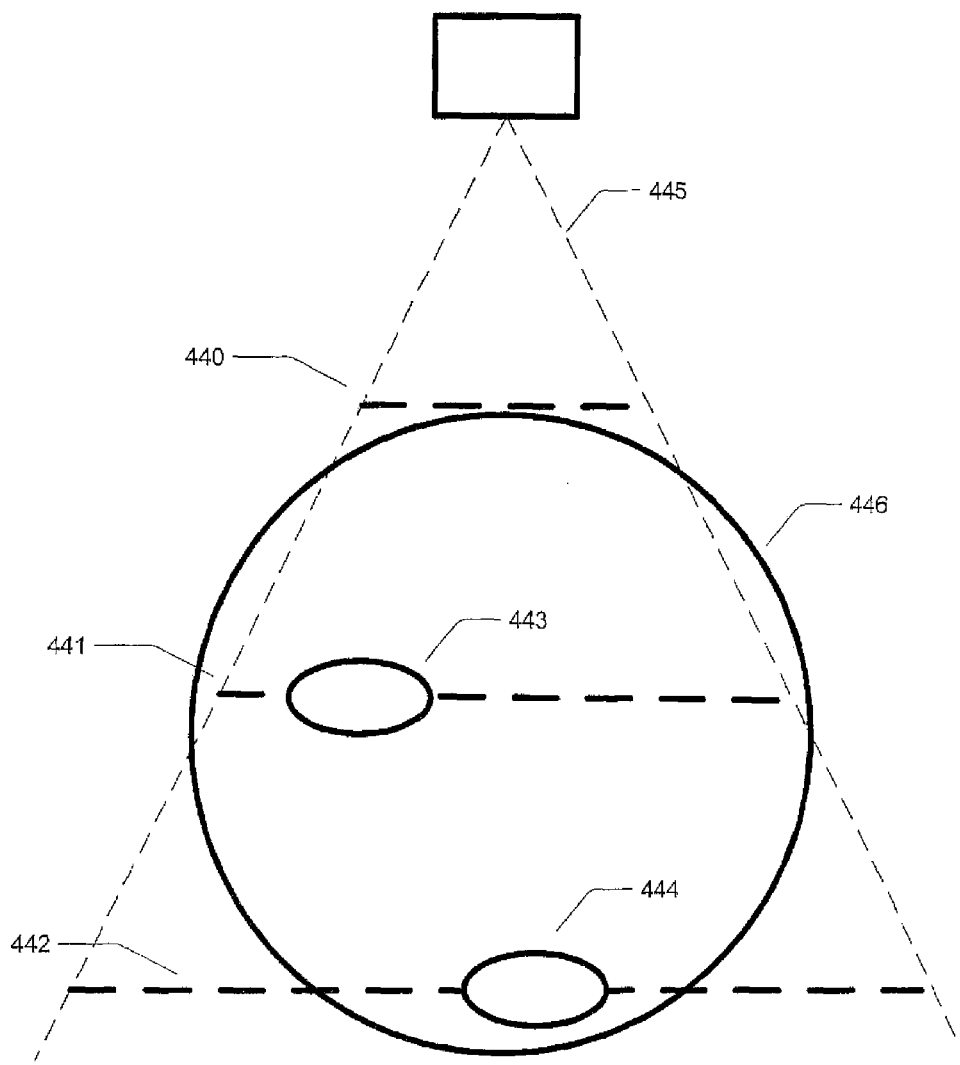
FIG. 10 shows the projection plane of the laser based vein enhancer of the present invention on a cross section of a patient's arm.

With reference to FIG. 10, a correction methodology is now described. The projection/imaging optical cone 445 of the MVE unit originates at the mirror of the MVE and diverges from there. The projection angle, for example, could be 60 degrees. A cross section of a patient's arm 446 is shown with a cross section of a first vein 443 shown at a first imaging plane 441 and a cross section of a second vein 444 shown at a second imaging plane 441. A projection plane 440 is also shown, which is approximately on the top surface of the arm 446 of the patient and represents where the image is displayed on the patient. In this example, the first imaging plane 441 is half way between the projection plane 440 and the second imaging plane 442. Due to the projection angle, the second imaging plane 442 is wider than the first imaging plane 441 which in turn is wider than the projection plane 440. In this example, the first vein and the second vein are each the same size. The first vein 443 as viewed at the first imaging plane 441 is one quarter the width of the first image plane 441. The second vein 444 as viewed at the second imaging plane 442 is one sixth the width of the second image plane 442. Accordingly when the images of the first and second veins are projected on the arm 446 on projection plane 440, the first vein 443 will appear to be one quarter the width of the projection plane 440, and the second vein 444 will appear to be one sixth the width of the projection plane 440. It should be noted that neither the projected image of the first vein 443 nor the projected image of the second vein 444 is accurately representative of the actual vein size.

In accordance with the present invention, a scaling process can be performed prior to transmitting the image of the veins onto the projection image plane 440. As previously described, the laser power of the 740 nm laser can be sequentially increased for each frame. A depth table correlating the depth of penetration of the 740 nm laser as a function of laser power can be pre-stored in memory. This depth information can then be used to correct the actual image size of the veins 443 and 444 prior to projecting their images onto projection plane 440. The correction algorithm can be straight forward trigonometry and therefore is not described herein.

FIG. 11 describes an embodiment which accurately projects the correct vein size regardless of the depth of the veins 443 and 444 within the patients arm. The optical path diverges at an angle 447 and hits a parabolic mirror 448 which is arranged to have a shape so that the optical beam 449 exiting off the mirror 448 is parallel and does not diverge. In this manner, the image of the veins 443 and 444 are both the same size, and when they are projected onto projection plane 440, the size of the vein images exactly matches that of the actual veins. As an alternative embodiment, a lens could be used instead of a parabolic mirror 448 for converting the diverging optical path to a parallel path.

As yet a further embodiment, it has been determined that increasing the wavelength of the laser light emitted from the laser 183 increases the depth of penetration into the flesh of the patient. This effect can be used to construct three dimensional images by increasing the wavelength of laser light emitted on sequential frames, thereby allowing the system to determine the depth of the veins (this is similar to the previous embodiment where the laser intensity was increased to obtain greater penetrations).

It should be noted that all embodiments herein have been described with a 740 nm laser 183 for imaging the veins/arteries. However, a broader range of wavelengths (700 nm to 1000 nm) could be utilized. Similarly, in the event a broader range of wavelengths are emitted by laser 183, the 740 nm photo detector 182 could be changed to a different wavelength to receive the associated wavelength (700 nm-1000 nm). Still further, the 630 nm (red) laser 180 has been utilized for displaying the image on a patient. The 630 nm (red) laser 180 could be replaced with any visible laser (generally in the range of 400 nm-700 nm). Still further, the single (red) laser 180 could be replaced with multiple lasers configured so that they project coaxially. For example, if red, green and blue lasers are utilized, full color images can be rendered.

It also should be noted that often description is made of identifying vein, and in some cases veins and/or arteries. The invention is not limited thereto. Any portion of the body containing blood would be appropriately imaged by the devices of this invention.

What is claimed is:

1. A three dimensional imaging system comprising:
a first laser configured to emit light at a first wavelength;
a second laser configured to emit light at a second wavelength being different from said first wavelength;
means for incrementally increasing an intensity of said first wavelength of light emitted by said first laser;
means for scanning said laser light from said first and second lasers onto a target;
a photodetector configured to receive and to be responsive to said first wavelength of light reflected from the target, said photodetector further configured to output a respective signal representing each of a plurality (N) of vein images, based on said received light, by differential absorption of said first wavelength, each of said plurality of vein images corresponding to an incrementally distinct depth beneath the target, formed by said incrementally increasing intensity of said first wavelength of light;
means for image processing configured to successively layer said plurality of vein images according to said incrementally distinct depth to create a processed vein image, said means for image processing further configured to transmit said processed vein image as a signal to said second laser; said second laser and said means for scanning configured to project said processed vein image onto the target.

2. The three-dimensional imaging system according to claim 1 further comprising a counter configured to cyclically count a present vein image of said plurality of vein images, being in the range of 1 to N.

3. The three-dimensional imaging system according to claim 2 wherein said means for incrementally increasing said intensity of said first wavelength of light is configured to incrementally increase said intensity linearly between said image count of 1 and said image count of N.

4. The three-dimensional imaging system according to claim 1 further comprising a combiner configured to combine said laser light from said first and second lasers.

5. The three-dimensional imaging system according to claim 4
wherein said means for scanning is further configured to scan said combined laser light in a raster pattern;
wherein said second wavelength of light comprises light at a wavelength of 630 nm; and
wherein said first wavelength of light comprises light at a wavelength of 740 nm.

6. The three-dimensional imaging system according to claim 4 further comprising a mirror configured to reflect said combined laser light to said means for scanning.

7. The three-dimensional imaging system according to claim 1 further comprising a means for sensing a position of said means for scanning relative to the target; and wherein said means for sensing in configured to communicate said position to said second laser.

8. The three-dimensional imaging system according to claim 1 wherein said means for image processing is further configured to replace each of said successively layered plurality of vein images of said processed vein image with a unique graphical representation.

9. The three-dimensional imaging system according to claim 8 wherein each said unique graphical representation comprises a unique pattern; and wherein each said unique pattern is from the group of patterns consisting of: a dot pattern, a diagonal striped pattern, and a checkered pattern.

10. The three-dimensional imaging system according to claim 8 wherein said unique graphical representation comprises a solid image having a uniquely different intensity for each of said successively layered plurality of vein images; and wherein said solid image for said first vein image at a first intensity of said incrementally increasing intensity of said first wavelength of light comprises a dark solid image, and wherein said solid image for said $N^{th}$ vein image comprises a lighter solid image.

11. The three-dimensional imaging system according to claim 8 wherein said second laser is further configured to emit light at a plurality of other wavelengths different from said first and second wavelengths; and wherein said unique graphical representation comprises projection by said second laser of a respective one of said wavelengths for each of said successively layered plurality of vein images.

12. A three dimensional imaging system comprising:
a first laser configured to emit light at a first wavelength;
a second laser configured to emit light at a second wavelength being different from said first wavelength;
means for incrementally increasing an intensity of said first wavelength of light emitted by said first laser;
a scanner configured to scan said laser light from said first and second lasers onto a target;
a photodetector configured to receive and to be responsive to said first wavelength of light reflected from the target, said photodetector further configured to output a respective signal representing each of a plurality (N) of vein images, based on said received light, by differential absorption of said first wavelength, each of said plurality of vein images corresponding to an incrementally distinct depth within the target, formed by said incrementally increasing intensity of said first wavelength of light;
an analog-to-digital converter configured to receive and to successively convert each of said plurality of vein images into a digital image;
a memory configured to receive and store each of said plurality of digital images;
an image formatter configured to receive said plurality of digital images from said memory and to successively layer said plurality of vein images according to said incrementally distinct depth to create a processed vein image, said image formatter further configured to output said processed vein image as a digital image;
a digital-to-analog converter configured to receive said processed vein image and to convert said digital image into an analog image signal, and to output said analog image signal to said second laser, said second laser and said scanner configured to scan said processed vein image onto the target.

13. The three-dimensional imaging system according to claim 12 further comprising means for sensing an instantaneous position of said scanner relative to the target for each of said plurality of vein images at said incrementally distinct depths; said means for sensing further configured for outputting said instantaneous position information for storage in said memory; and wherein said second laser and said scanner are further configured to receive said position information from said memory and to scan said plurality of vein images according to said position information to be visibly focused on the target.

14. The three-dimensional imaging system according to claim 13 further comprising a counter configured to cyclically count a present vein image of said plurality of vein images, being in the range of 1 to N images, said present vein image count of said counter configured to signal said means for incrementally increasing said intensity of said first wavelength of light emitted by said first laser to cause a subsequent incremental increase in said intensity.

15. The three-dimensional imaging system according to claim 14 wherein said means for incrementally increasing said intensity of said first wavelength of light is configured to incrementally increase said intensity linearly between said image count of 1 and said image count of N.

16. The three-dimensional imaging system according to claim 15 further comprising a combiner configured to combine said laser light from said first and second lasers.

17. The three-dimensional imaging system according to claim 15 wherein said image formatter is further configured to replace each of said successively layered plurality of vein images of said processed vein image with a unique graphical representation.

18. The three-dimensional imaging system according to claim 17 wherein each said unique graphical representation comprises a unique pattern; and wherein each said unique pattern is from the group of patterns consisting of: a dot pattern, a diagonal striped pattern, and a checkered pattern.

19. The three-dimensional imaging system according to claim 17 wherein said unique graphical representation comprises a solid image having a uniquely different intensity for each of said successively layered plurality of vein images; and wherein said solid image for said first vein image at a first intensity of said incrementally increasing intensity of said first wavelength of light comprises a dark solid image, and wherein said solid image for said $N^{th}$ vein image comprises a lighter solid image.

20. The three-dimensional imaging system according to claim 19 wherein said second laser is further configured to emit light at a plurality of other wavelengths different from said first and second wavelengths; and wherein said unique graphical representation comprises projection by said second laser of a respective one of said wavelengths for each of said successively layered plurality of vein images.

21. A three dimensional imaging system comprising:
a first laser configured to emit light at a first wavelength;
a second laser configured to emit light at a second wavelength being different from said first wavelength;
means for incrementally increasing an intensity of said first wavelength of light emitted by said first laser;
a scanner configured to scan said laser light from said first and second lasers onto a target;
a photodetector configured to receive and to be responsive to said first wavelength of light reflected from the target, said photodetector further configured to output a respective signal representing each of a plurality (N) of vein images, based on said received light, by differential absorption of said first wavelength, each of said plurality of vein images corresponding to an incrementally distinct depth beneath the target, formed by said incrementally increasing intensity of said first wavelength of light;
an analog-to-digital converter configured to receive and to successively convert each of said plurality of vein images into a digital image;
a memory configured to receive and store each of said plurality of digital images;
a stereo display device;
a computer and imaging software configured to receive each of said plurality of digital images from said memory and to provide a three-dimensional rendering of the veins in said vein images to said stereo display device, for display of the veins thereon.

* * * * *